US006326465B1

(12) United States Patent
Hess

(10) Patent No.: US 6,326,465 B1
(45) Date of Patent: Dec. 4, 2001

(54) IMMUNOMODULATORY POLYPEPTIDES DERIVED FROM THE INVARIANT CHAIN OF MHC CLASS II

(75) Inventor: Allan D. Hess, Cockeysville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/028,274

(22) Filed: Feb. 24, 1998

Related U.S. Application Data
(60) Provisional application No. 60/039,032, filed on Feb. 24, 1997.

(51) Int. Cl.$^7$ .......................... A01N 63/00; A01N 37/18; A61K 38/17
(52) U.S. Cl. .................. 530/324; 424/93.2; 424/93.7; 424/185.1; 514/2; 530/325; 530/326; 530/327; 530/328; 530/329; 530/330; 530/331; 530/350
(58) Field of Search .......................... 530/350, 324–331; 514/2; 424/183.1, 93.2, 93.7

(56) References Cited

U.S. PATENT DOCUMENTS
5,559,028 * 9/1996 Humphries et al. .
5,827,516 * 10/1998 Urban .

OTHER PUBLICATIONS

Snaderson et al PNAS 92:7217–7221, 1995.*
Malcherek et al J. Exp. Med. 181:527–536, 1995.*
Allan D. Hess et al. "Specificity of Effector T Lymphocytes in Autologous Graft–Versus–Host Disease: Role of the Major Histocompatibility Complex Class II Invariant Chain Peptide" Blood vol. 89, No. 6 (Mar. 15), 1997: pp. 2203–2209.
Han Zhang et al. "The Role of Cyclosporine–Induced Autoreactive T Lymphocytes in Solid Organ Allograft Survival and Chronic Rejection" Transplantation Articles, vol. 60, 115–122 No. 2, Jul. 27, 1995.
Allan D. Hess "The Immunobiology of Syngeic/Autologous Graft–versus–Host Disease" Graft–vs.–Host Disease Chapter 20, pp. 561–586 (1997).
Nucleic Acids Research, ISSN 0305–1048 IRL Press, 1985, vol. 13, pp. 8827–8841 Kudo et al.
Lena Claesson et al. "cDNA clone for the human invariant λ chain of class II histocompatibility antigens and its implications for the protein structure" Proc. Natl. Acad. Sci., USA, vol. 80, pp. 7395–7399, Dec. 1983 pp. 7395–7399.
Accession AA170258 (1996).
Accession K01144, Medline 84170234 (1993).
Accession AA822778 (Feb. 1998).
Accession X03339—GenBank (1985).
Accession X03340, Medline 86093681 (1985).
Accession M31952 (1989).
Accession M13555, Medline 86233451 (1986).
Accession M13556, Medline 86233451 (1986).
Accession M13557, Medline 86233451 (1986).
Accession M13558, Medline 86233451 (1986).
Accession M13560, Medline 86233451 (1994).
Accession AA646546 (Oct. 1997).
Accession AA762678 (1996).
Accession M13559, Medline86233451 (1986).

* cited by examiner

*Primary Examiner*—David Saunders
*Assistant Examiner*—Amy DeCloux
(74) *Attorney, Agent, or Firm*—Banner & Witcoff, Ltd.

(57) ABSTRACT

Polypeptides derived from a proteolytically cleaved portion of the invariant chain of MHC class II, termed CLIP, have been found to have immune modulatory properties. Depending on the portions of CLIP administered, immune responses can be either enhanced or suppressed. In addition, these portions can be used to cause weakly immunogenic proteins more strongly immunogenic. The polypeptides can be used directly to modulate the immune response, as can antibodies directed to particular portions of the CLIP polypeptides. Alternatively, polynucleotides encoding either the polypeptides of the antibodies can be administered to cause in situ generation of the immunomodulatory polypeptide or antibodies.

39 Claims, 6 Drawing Sheets

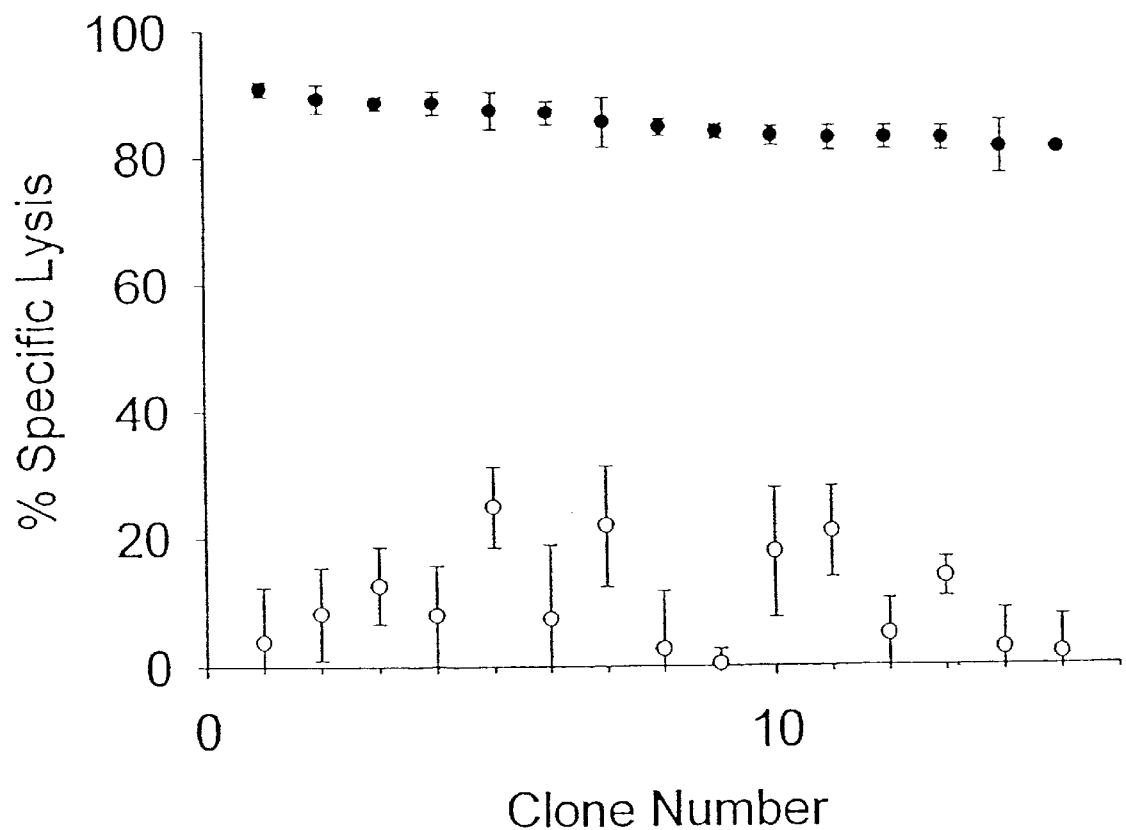

FIG. 4

```
   1 ctgcaggggg ggggggggggg gggggaca ttggctcttc cttggggagt gatgcacagg
  61 aggagaagca ggagctgtcg ggaagatcag aagccagtca tggatgacca gcgcgacctt
 121 atctccaaca atgagcaact gcccatgctg ggccggcgcc ctggggcccc ggagagcaag
 181 tgcagccgcg gagcctgta cacaggcttt tccatcctgg tgactctgct cctcgctggc
 241 caggccacca ccgcctactt cctgtaccag cagcagggcc ggctggacaa actgacagtc
 301 acctcccaga acctgcagct ggagaacctg cgcatgaagc ttcccaagcc tcccaagcct
 361 gtgagcaaga tgcgcatggc caccccgctg ctgatgcagg cgctgcccat gggagccctg
 421 cccccagggc ccatgcagaa tgccaccaag tatgccaaca tgacagagga ccatgtgatg
 481 cacctgctcc agaatgctga cccctgaag gtgtacccgc cactgaaggg gagctttccg
 541 gagaacctga gacacctta aacaccatg gagaccatag actggagact cctgaaggt ctttgagagc
 601 tggatgcacc attggctcct gttgaaatg agcaggcact cctggagca aaagcccact
 661 gacgctccac cgaaagagtc actggaactg gaggacccgt ctttctgcct gggtgtgacc
 721 aagcaggatc tgggcccagt cccatgtgta gagcagcaga ggcggtcttc aacatcctgc
 781 cagcccaca cagctacagc ctcatccat cccagccc ccagccccctc cccatctcc
 841 caccctgtac ctcatcccat gagacccgtg tgcctggctc tttcgtcacc cttggacaag
 901 acaaaccaag tcggaacagc agataacaat gcagcaaggc cctgctgccc aatctccatc
 961 tgtcaacagg ggcgtgaggt cccaggaagt ggccaaaagc tagacagatc cccgttcctg
1021 acatcacagc agcctccaac acaaggctcc aagacctagg ctcatggacg agatgggaag
1081 gcacagggag aagggataac cctacaccca gacccaggc tggacatgct gactgtcctc
1141 tcccctccag cctttgcct tgcttttct agcctattta cctgcaggct gagccactct
1201 cttcccttc cccagcatca ctcccaagg aagagccaat gtttccacc catcccctcc
1261 cccccccccc ccccccccc cctgcag
```

FIG. 5

```
   1 cagcagcagc agcagcagca gcaccagcag cacttggggg aaaagctaga ggctagagtc
  61 atggatgacc agcgcgacct catctctaac catgagcagc tgcccatcct gggccagcgt
 121 gctagagccc cagaaagcaa ttgcaaccgt ggagtcctgt acaccagtgt ctctgtcctg
 181 gtggctctgc tcttggctgg gcaggccacc actgcttact tcctgtacca gcagcagggc
 241 cgcctggaca agctgaccgt cacctcccag aacctgcaaa tggagaacct tcgcatgaag
 301 cttccgaaat ctgccaaaac tgtgagcccg atgcgcatgg ctactccctt gctgatgcgc
 361 ccactgtcca tggataacat gctccaagcg cccgtgaaga atgttaccaa gtatggcaac
 421 atgacccagg accacgtgat gcacctgctt acgaagtctg gaccgtgaa ctaccacag
 481 ctgaagggga gcttcccgga gaatctgaag cacctgaaga actctatgaa tggtctggac
 541 tggaaggtct ttgagagctg gatgaaacag tggctgtttgt ttgaaatgag caagaactcc
 601 ctggaggaga agcagcccac ccagactcca cctaaagtat tgaccaagtg ccaggaagaa
 661 gtcagccaca tccctgatgt ccacccgggg gcgttccgtc ccaagtgtga tgagaacggt
 721 aactatatgc cactccagtg ccatcccaag acctgctact gctggtgtgt gttcccccaac
 781 ggcactgagg tccctcacac caagagccgc actgccata actgcagtga gccactggac
 841 atggaagacc catcttctgg cctggagtg accaagcagg atatgggcca aatgttcttg
 901 tgaagacaga agccagctct gcacggcggc agctcccctg ctcccagcc cttcttacac
 961 tccctaacat cacaccccat ttcccgtctt ccctgcaccct ggggcttgag actggtatct
1021 gcttcaccgt ccctggacac aacaaatgaa acggaacag aatgagaaca ctggagggag
1081 ggccttgctg cctaccccca tctaagggac ccccattct gacccattag cagtctttaa
1141 tgtggggctc tgagatctag gcccactgac agggataggg gatgccctac ccttaatcta
1201 ggctggatac atttgctgtc ttctcaagga agaggccaag cctcccagc aacccttcct
1261 catgtcctgc cgacgcccct gggatccctg ctcagccaag cttgtcagca gcctgtagga
1321 ccatggttca cgtgacaata aaagtagaa ggt
```

IMMUNOMODULATORY POLYPEPTIDES DERIVED FROM THE INVARIANT CHAIN OF MHC CLASS II

This application claims the benefit of U.S. Ser. No. 60/039,032 filed Feb. 24, 1997, the disclosure of which is expressly incorporated herein.

This invention was made with support from the National Institutes of Health, Grant Nos. AI24319 and CA15396. The U.S. government therefore retains certain rights in the invention.

TECHNICAL FIELD OF THE INVENTION

This invention is related to the field of immunology. More particularly it is related to the field of modulation of immune responses, in particular induction of anti-tumor immune responses.

BACKGROUND OF THE INVENTION

Recent studies in man and in rat show that the administration of Cyclosporine (CsA) after autologous or syngeneic BMT induces an autoimmune syndrome resembling graft-vs-host disease (GVHD).[1-5] This syndrome is termed syngeneic or autologous GVHD. Results from animal studies suggest that syngeneic GVHD has significant antitumor activity.[11,12] Moreover, the antitumor effect of this autoaggression syndrome can be enhanced by the administration of cytokines that upregulate the expression of the MHC Class II target antigen on the tumor cell.[6,7] Clinical trials are currently underway to evaluate the antitumor immunotherapeutic potential of autologous GVHD in man.[8-12]

Thee is a need in the art for additional tools and methods to modulate the anti-tumor immune response found in syngeneic GVHD.

SUMMARY OF THE INVENTION

It is an object of the present invention to provide polypeptides for stimulating an immune response.

It is another object of the present invention to provide polypeptides for suppressing an immune response.

It is an object of the present invention to provide methods of modulating an immune response.

Another object of the invention is to provide a vaccine for inducing an immune response to an antigen.

Another object of the invention is to provide method for screening compounds to identify those which will modulate a cellular immune response.

Another object of the invention is to provide an antibody which is useful for suppressing an immune response.

Another object of the invention is to provide a method to monitor cyclosporin therapy.

It is still another object of the invention to provide polynucleotide molecules which encode CLIP polypeptides.

These and other objects of the invention are achieved by one or more of the embodiments described below. In one embodiment a polypeptide is provided. The polypeptide comprises a first and second segment. The first segment consists of amino acid residues of the invariant chain of MHC class II selected from SEQ ID NO: 1 and comprises the sequence VSP. The second segment comprises an antigen. Alternatively the first segment consists of amino acid residues of the invariant chain of MHC class II selected from SEQ ID NO: 5 and comprises the sequence VSK.

According to another embodiment of the invention a polypeptide is provided which consists of a segment of the invariant chain of MHC class II. The segment contains 3 to 28 contiguous amino acid residues selected from SEQ ID NO: 1 and comprises the sequence VSP. Alternatively, the segment contains 3 to 28 contiguous amino acid selected from SEQ ID NO: 5 and comprises the sequence VSK.

In another embodiment of the invention a method is provided for modulating an immune response. The method comprises the step of contacting T cells with a polypeptide. The polypeptide comprises a segment of the invariant chain of MHC class II. The segment consists of 3 to 29 contiguous amino acid residues selected from SEQ ID NO: 1 and comprises the sequence VSP. Alternatively, the segment consists of 3 to 29 contiguous amino acid residues selected from SEQ ID NO: 5 and comprises the sequence VSK.

According to another aspect of the invention, a vaccine is provided for inducing an immune response to an antigen. The vaccine comprises a polypeptide which comprises a first and second segment. The first segment consists of amino acid residues of the invariant chain of MHC class II selected from SEQ ID NO: 1 and comprises the sequence VSP. The second segment comprises an antigen. Alternatively, the first segment consists of amino acid residues of the invariant chain of MHC class II selected from SEQ ID NO: 5 and comprises the sequence VSK. The polypeptide is suspended in a pharmaceutically acceptable carrier.

In still another aspect of the invention, a method is provided for screening compounds to identify those which will modulate a cellular immune response. The method comprises the step of contacting a CLIP polypeptide as shown in SEQ ID NO: 1, or a portion of a CLIP polypeptide comprising VSP, with an $\alpha/\beta$ T Cell Receptor and a test compound. The amount of binding of the CLIP polypeptide (or portion) bound to the $\alpha/\beta$ T Cell Receptor is determined. A test compound which reduces the amount of binding is identified as a candidate immunosuppressant. A test compound which increases the amount of binding is identified as a candidate immunostimulant.

Another embodiment of the invention is an antibody. The antibody specifically binds to a CLIP polypeptide as shown in SEQ ID NO: 1 or SEQ ID NO: 5, and inhibits binding of the CLIP polypeptide to MHC class II or T Cell Receptor.

In still another aspect of the invention a polypeptide is provided. The polypeptide comprises a segment of the invariant chain of MHC class II selected from SEQ ID NO: 1. However, the segment does not contain the sequence VSP. Alternatively, the segment of the invariant chain of MHC class II is selected from SEQ ID NO: 5, and the segment does not comprises the sequence VSK.

In still another embodiment of the invention, a method is provided for modulating an immune response. T cells are contacted with a polypeptide comprising a segment of the invariant chain of MHC class II. The segment consists of amino acid residues selected from SEQ ID NO: 1. However, the segment does not contain the sequence VSP. Alternatively, the segment consists of amino acid residues selected from SEQ ID NO: 5 and wherein the segment does not contain the sequence VSK.

In even another embodiment of the invention a polynucleotide is provided. The polynucleotide encodes any of the CLIP derived polypeptides described herein. The CLIP derived polypeptides may be the full-length CLIP polypeptide of 29 amino acids, a truncated version of CLIP having an N-terminal, a C-terminal or an internal deletion.

A method of monitoring cyclosporin therapy is yet another aspect of the invention. The method involves testing a sample of T cells for the ability to bind to CLIP polypeptide as shown in SEQ ID NO: 5. The T cells are isolated from a patient receiving cyclosporin therapy. The amount of T cells which bind to CLIP polypeptide indicate the patient's responsiveness to cyclosporin.

These and other embodiments of the invention, which are described more fully below, provide the art with tools and methods for treating a variety of immune and non-immune based diseases. In addition, tools are provided for discovering small molecules with immune modulatory activity.

BRIEF DESCRIPTION OF THE DRAWINGS

FIG. 3: Lytic activity of SVGHD effector clones. The lysis of Lewis strain rat target cells loaded with either the parent BN allopeptide (SEQ ID NO: 15) or the chimeric construct (SEQ ID NO:14), by 15 syngeneic GVHD effector clones.

FIG. 4: Human polynucleotide sequence encoding the invariant chain of MHC class II (SEQ ID NO:16).

FIG. 5: Rat polynucleotide sequence encoding the invariant chain of MHC class; II (SEQ ID NO: 17).

DETAILED DESCRIPTION

Figure 1:
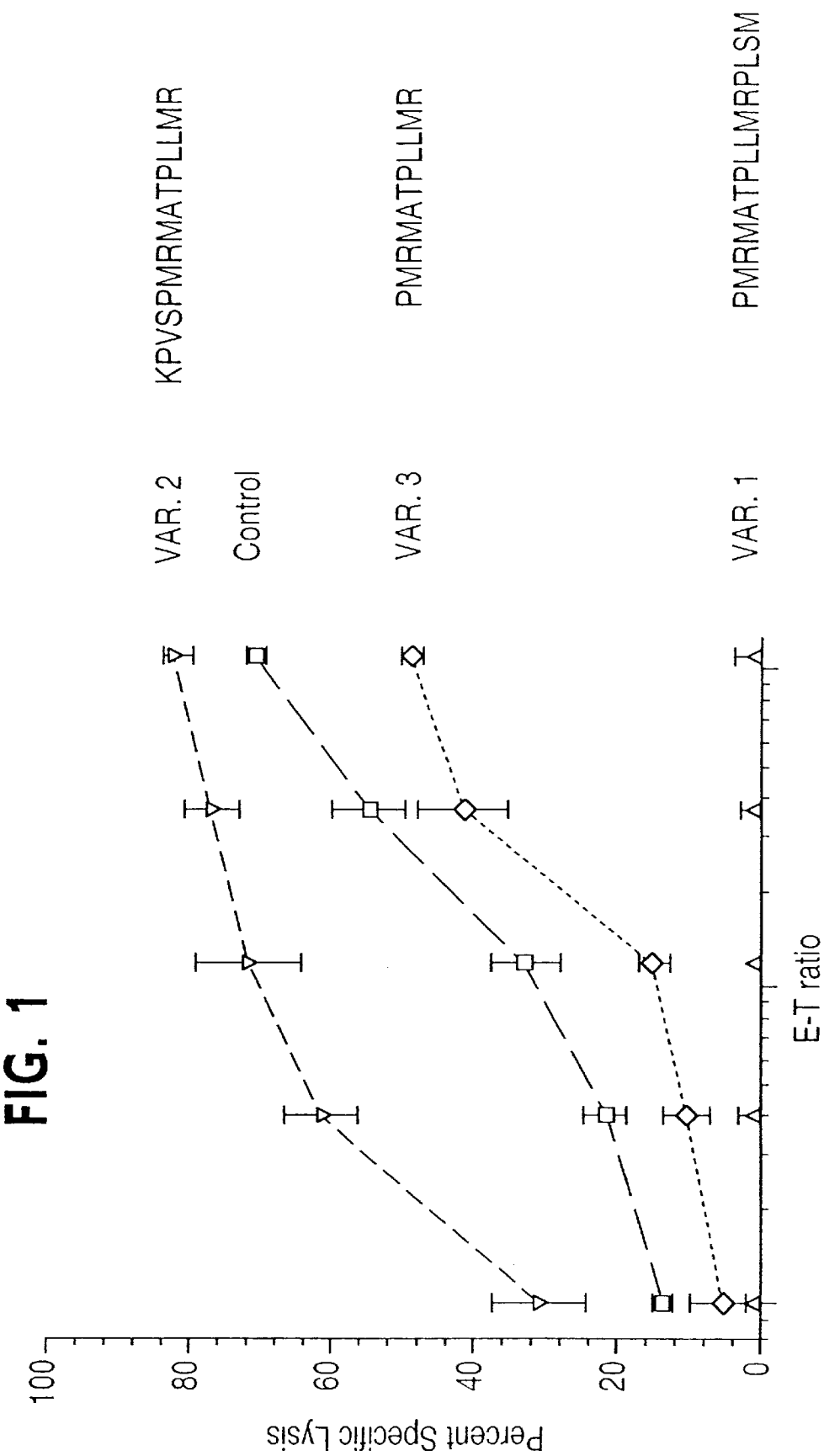
FIG. 1. Graph showing comparison of percent specific lysis conferred by truncated variants of CLIP. Lewis syngeneic PHA blasts were force-loaded with the truncated variants of CLIP (10 μmol/L, 1 hr, 4° C.) prior to assay. Effector T cells (nylon wool nonadherent) were derived from animals with syngeneic GVHD that were clonally expanded in thymectomized secondary Lewis recipients.
Figure 2A:
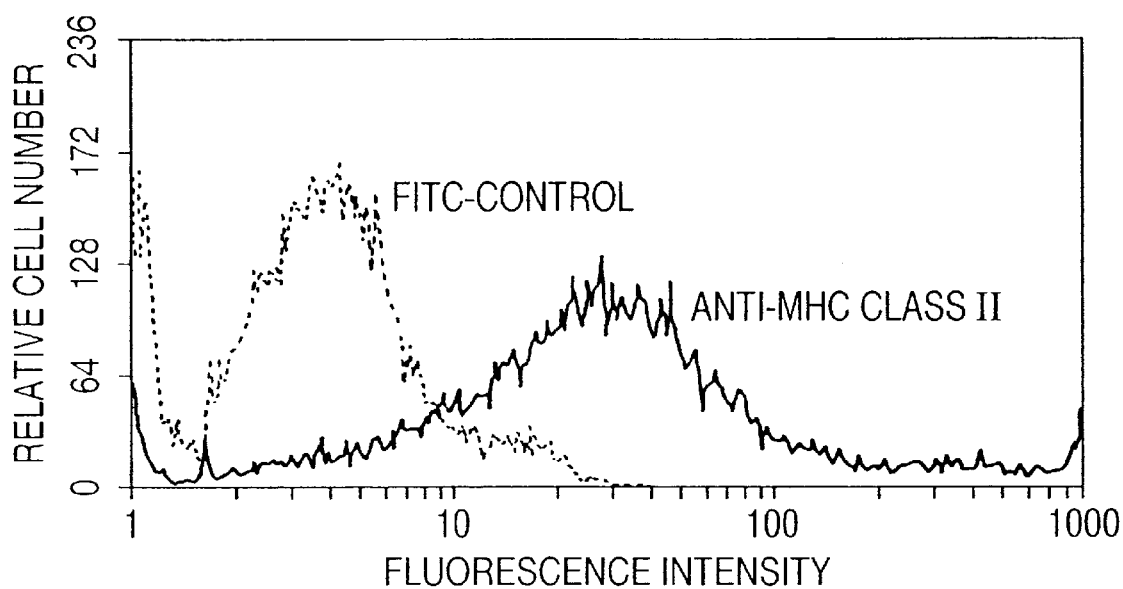
FIG. 2. Cell surface expression of CLIP and MHC Class II determinants on lymphoblasts and the T47D breast cancer cell line. PHA lymphoblasts (identified by electronic gating for cell size and scatter) and the T47D cell line were assessed flow cytometrically for expression of the MHC Class II determinants and for cell surface CLIP. MHC Class II expression was assessed by staining the cells with murine anti-HLA DR followed by counterstaining with FITC conjugated sheep anti-mouse IgG. Control cells were pretreated with normal mouse serum prior to counterstaining (A, lymphoblasts; C, T47D). CLIP expression was assessed by staining with affinity purified rabbit anti-CLIP antibody and counterstaining with FITC conjugated goat anti-rabbit IgG. As controls, the lymphoblasts and the T47D cell line were pretreated with rabbit prebleed IgG prior to counterstaining with FITC goat anti-rabbit IgG. (B, lymphoblasts; D, T47D breast cancer cell line).
Figure 2B:
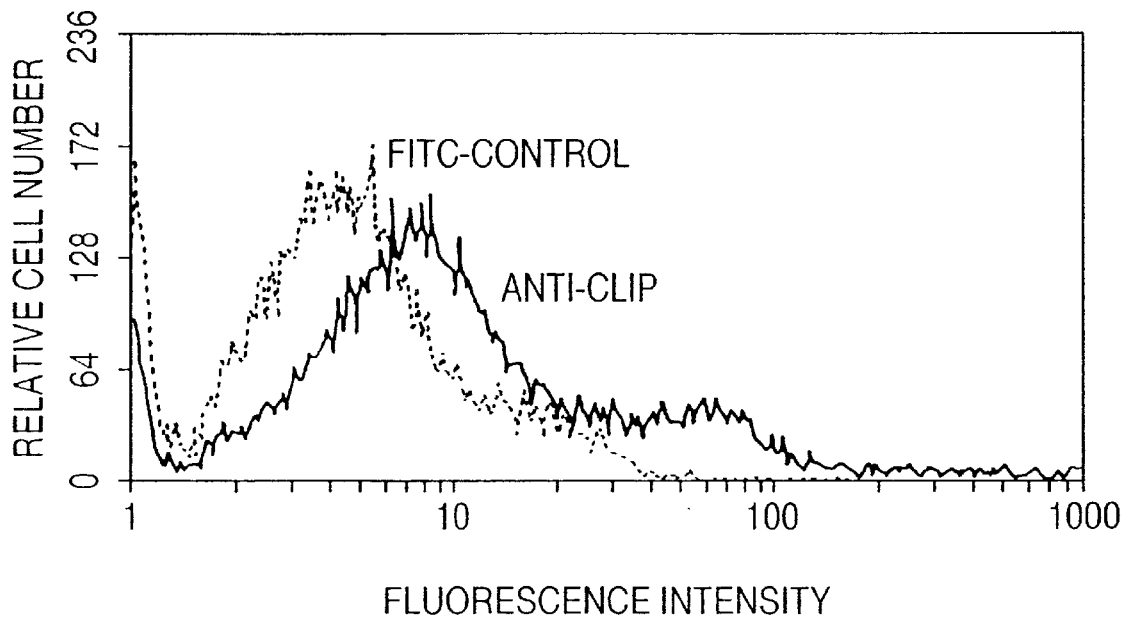
Figure 2C:
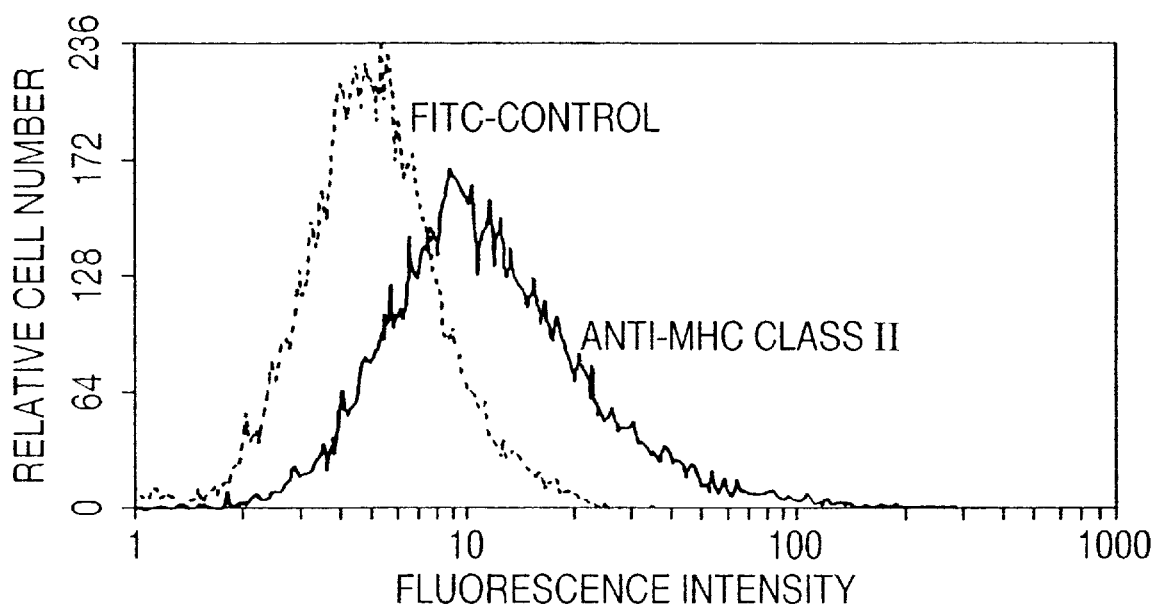
Figure 2D:
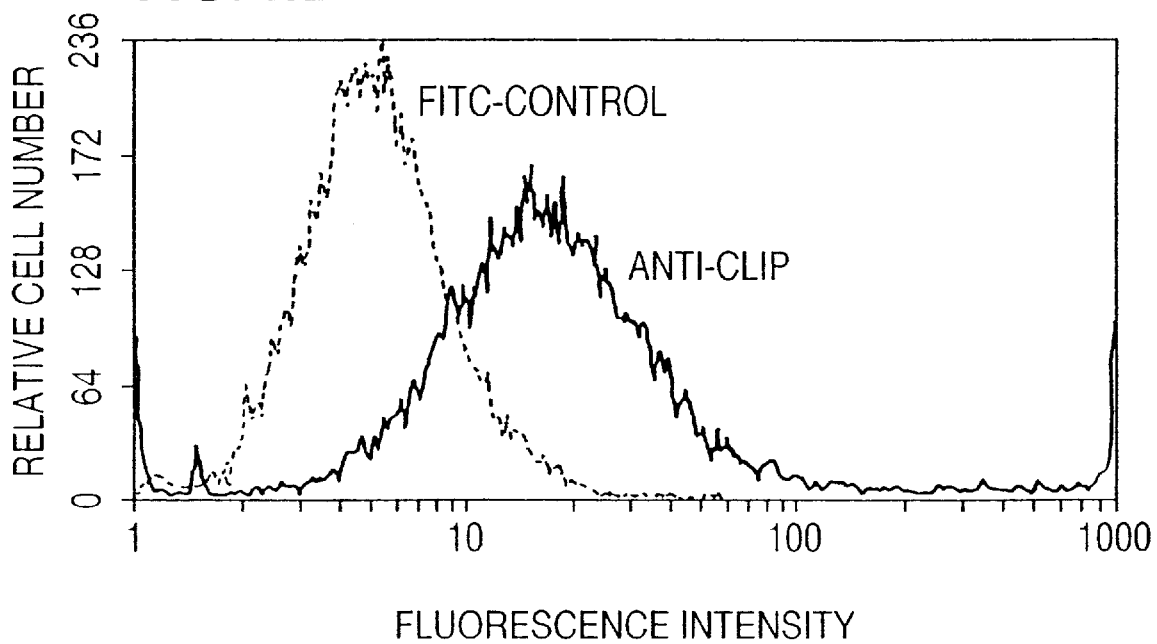

It is a discovery of the present inventor that CLIP polypeptide, a portion from the invariant chain, has dramatic modulatory effects on the immune system of mammals. When contacted with T lymphocytes, CLIP polypeptide can function as a superantigen, enhancing the activity of cytolytic T cells or B cells. For example, in the context of graft versus host disease (GVHD) CLIP can enhance autoreactive T lymphocyte-mediated tumor cell killing. Similarly, CLIP variants containing the MHC class II binding domain and the N-terminal flanking region also can enhance tumor cell killing. Conversely, CLIP variants containing the MHC class II binding domain and the C-terminal flanking region do not have such activity.

Moreover, it has been found that the CLIP polypeptide can be used to overcome MHC restriction. Chimeric fusion polypeptides which comprise the MHC class II binding site of CLIP permit the promiscuous recognition of antigens which are normally not recognized by target autoreactive T cells. Thus chimeric fusion polypeptides can be made using CLIP, or truncated variants thereof, to modulate the immune response to the non-CLIP fusion partner. Thus if an antigen is used, such as a viral antigen or a tumor-associated antigen such as her2/neu, the immune response to that antigen can be increased. Preferably, the CLIP fusion partner comprises the segment PVSP (SEQ ID NO:1) or PVSK (SEQ ID NO:11), preferably KPVSP (SEQ ID NO:1) or KPVSK (SEQ ID NO:11), and more preferably PKSAKPVSP (SEQ ID NO:1) or PKPPKPVSK (SEQ ID NO:6). Typically each fusion partner comprises at least 3 amino acids, and preferably at least 6 amino acids, and more preferably at least 9 amino acids. The fusion polypeptides can be formed by genetic engineering, synthetic chemistry, or by covalent bonding of portions of naturally occurring proteins. By judicious selection of the portion of CLIP utilized, immune response enhancement or suppression can be effected. It is believed that the N-terminal flanking region of the MHC class II binding region of CLIP is stimulatory and the C-terminal region is suppressive. See FIG. 1. CLIP and the N-terminal and C-terminal flanking regions of CLIP from other mammalian species can also be used.

Polypeptides useful for stimulating or suppressing immune responses need not comprise an antigen. Other biologically active proteins may be used as fusion partners, such as toxins, reporter proteins, carrier antibodies, and enzymes. Macromolecules, such as polysaccharides, polyacrylamide, solid matrices, radiolabels, and fluorescent labels may also be conjugated or bound to the polypeptides. In addition, polypeptides which comprise all or portions of the naturally occurring CLIP molecule may be useful as suppressive or stimulatory molecules without attachment to other moieties.

The polypeptides of the present invention can be administered to patients to modulate immune responses. Preferably the patients are cancer patients. More preferably the patients are bone marrow transplant recipients. More preferably the patients are bone marrow transplant recipients who are also receiving cyclosporin. Other patients who require modulation of immune responses, including those with hematological disorders, viral infections, and autoimmune diseases, such as lupus, can also benefit from polypeptide therapy. Modulated immune responses include enhancing and suppressing either cell-mediated or humoral responses. The binding of CLIP to T cells may induce T helper cells which produce cytokines which promote B cells to make antibodies and proliferate.

It is believed that the polypeptides of the invention interact with T cells to exert their effect, specifically with CD8+ T cells. Such cells can be contacted ex vivo and reinfused to the patient. Alternatively the polypeptide can be administered by any means known in the art such that the polypeptide reaches the T cells. This may be by intraperitoneal, intravenous, subcutaneous, or intramuscular injections. This may be by injestion of oral formulations. This may be by administration to the individual of a recombinant construct which encodes the polypeptide of the present invention. Expression in vivo of the polypeptides may prove a more efficient means of delivery. Liposomes or other particulate formulations may be used, comprising a carrier molecule, to protect and/or target the polypeptides or polynucleotides to the T cells. Cells such as dendritic cells can be transfected ex vivo with such polynucleotides and administered to a patient to obtain expression of the polypeptides of the invention.

Thus the polypeptides of the present invention when suspended in a pharmaceutically acceptable carrier form a vaccine for inducing an immune response. The vaccine can further comprise immune adjuvants such as BCG which are known in the art. Alternatively, the vaccine may be a genetic vaccine which comprises a polynucleotide encoding one or more of the polypeptides of the present invention.

Having determined the binding of CLIP polypeptides to α/β chains of the T cell receptor, this interaction can be used as a means of identifying useful drugs. Compounds, whether small molecules, polymers, oligonucleotides, peptides, or derivatives of these, can be contacted with a CLIP polypeptide and an α/β T Cell receptor. Libraries of such molecules can also be screened. The effect of the compound on the binding interaction can be determined. Thus compounds which inhibit, displace, or prevent binding of the two binding partners are candidate immunosuppressants. Compounds which increase binding of the two binding partners are candidate immunostimulants. The binding assay can also be performed in the presence of other molecules, particularly MHC class II molecules. The format of the assay can be varied as is convenient. One binding partner can be attached to a solid support, and the other partner can be labeled, such as with a radiolabel, fluorescent label, etc. The amount of the labeled partner which is found either remaining bound or unbound can be determined. Antibodies can be used to quantitate the binding partner which is not attached to the solid support. The solid support may be, for example, a microtiter dish, or beads which are packed in a column. Any means known in the art for performing such assays can be utilized.

Antibody preparations according to the present invention can be monoclonal or polyclonal. Preferably they are monospecific and bind only to a portion of CLIP polypeptide which is either the MHC class II binding domain, the N-terminal flank, or the C-terminal flank. Such antibodies can be used in drug screening assays, for example, to quantitate the amount of binding partners bound. Alternatively, such antibodies can be used therapeutically to inhibit the binding of endogenous CLIP to MHC class II or to α/β T cell receptor.

Polynucleotides according to the present invention may have any sequence which encodes the desired polypeptide sequence. The full length CLIP may be encoded, or portions of CLIP, or either of those fused to another polypeptide may be encoded. The nucleotide sequence may comprise the natural sequence found in a mammal. See FIGS. 4 and 5, for example. Alternatively, any equivalent sequence (by virtue of the degeneracy of the genetic code) can be used. The polynucleotides desirably comprise a promoter to render transcription possible, and a translation initiation site. More preferably the promoter is regulatable, such as with an exogenous substance such as tetracycline. The polynucleotides can be present in a vector for introduction into cells. The polynucleotide may be integrated in the genome of cells which will be infused into a patient, for example.

Because cyclosporin induces the T cell population to which CLIP binds, CLIP binding can be used as a method of monitoring cyclosporin therapy, by determining the amount of, or changes in the amount of such T cell populations. T cells can be isolated from a patient receiving cyclosporin therapy and either assayed directly or fractionated to enrich for the population of CD8+ cells. The amount of cells binding to CLIP can be determined, for example using radiolabeled CLIP polypeptide. The cells can be incubated with CLIP polypeptide and the excess non-binding CLIP polypeptide can be removed. The amount of CLIP polypeptide bound to the cells can then be determined. Alternatively, anti-CLIP antibodies can be used to label the cells which have CLIP bound. The labeled cells can be quantitated by any means known in the art. One particular method employs flow cytometry, as shown in FIG. 2. Other methods can be used as is convenient.

Recent studies in our laboratory suggest that there are subsets of cells that can be separated based on their dependency for either the N-terminus or C-terminus of CLIP. Thus, cells can be separated using CLIP polypeptides which have either the N- or, C-terminal portions. For example, such portions can be attached to a solid support and used to pan cells from a mixture of cells. This may be useful diagnostically to determine the status of a patient's immune response. It may also be useful preparatively, to obtain relatively homogenous populations of T cells.

The antitumor effect which has been observed using CLIP polypeptides alone, or fused to tumor antigens, appears to be enhanced by the administration of recombinant γ-interferon. On the other hand, α-interferon, although less effective than γ-interferon, also potentiates the antitumor activity of autologous GVHD.[24] Such cytokines can be administered with CLIP polypeptides or polynucleotides encoding CLIP, simultaneously or sequentially.

The polynucleotide of the present invention may be DNA or RNA, and may further comprise a sequence which directs the secretion of the encoded polypeptide from the cell. When the polynucleotide is DNA, it can also be a DNA sequence which is itself non-replicating, but which can be inserted into a replicating plasmid vector. The polynucleotide may be engineered such that it is not integrated into the host cell genome. Alternatively, the polynucleotide may be engineered for integration into the chromosome, preferably the expression of the polypeptide will be regulatable. Such regulatable gene expression systems having in vivo applicability are known in the art, and may be used in the present invention. For example, selective killing of transfected cells may be mediated by including in the polynucleotide or vector a gene sequence encoding a protein, such as HSV thymidine kinase. The thymidine kinase gene acts as a suicide gene for transfected cells if the patient is exposed to gancyclovir. Thus, if expression of the encoded peptides of the invention is too high, gancyclovir may be administered to reduce the percentage of cells expressing the peptides.

Depending on the compound contained in the pharmaceutical compositions of the present invention, the length of the administration term may vary. For example, if the pharmaceutical composition comprises a naked DNA sequence operatively encoding the polypeptide, cells incorporating the polynucleotide may produce the polypeptide for at least one month. Alternatively, if transitory expression of the polypeptide is preferred, the composition of the invention may include a DNA or RNA sequence operatively encoding the polypeptide, whereby cells containing the DNA or RNA produce the polypeptide for less than about 20 days, usually less than about 10 days, and often less than 3 or 5 days (Felgner et al., U.S. Pat. No. 5,589,466).

Preferably, the compounds of the present invention are polypeptides. The polypeptides are preferably 30 amino acids or less, more preferably 20 amino acids or less, and comprise amino acid sequences derived from either the MHC class II invariant chain or SEB that enable the peptide to interact with both MHC class II molecules and the T cell α/β receptor. As one of ordinary skill in the art is aware, conservative substitutions may be made in the amino acid sequence of the disclosed peptides without losing functionality. These substitutions are well known and are based upon the charge and structural properties of each amino acid.[22] Such functionally equivalent peptides are also encompassed in the present invention. Desirably the core amino acid sequence for modulating the immune response is not changed.

In the instance that the pharmaceutical composition comprises a nucleic acid, it is also well known to those skilled in the art that, due to the degeneracy of nucleolide coding sequences, a number of different nucleic acid sequences may encode the same peptide. The nucleotide sequences of the present invention may also be altered by mutations such as substitutions, additions or deletions that provide for functionally equivalent peptide sequences. Functionality can be determined as shown in FIG. 1, for example.

The compounds of the present invention can be synthesized by any means known in the art. For instance, both DNA and RNA can be prepared directly using automated nucleic acid synthesis equipment, PCR, cloning, or any combination of such techniques. When the polynucleotide is RNA, it can be readily prepared from the corresponding DNA template using an in vitro expression system known in the art. The present peptides may also be prepared using recombinant DNA technology from the corresponding nucleic acids. Alternatively, the peptides of the invention may be prepared using chemical synthesis. A helpful review of known peptide synthesis protocols and factors to consider when synthesizing a peptide for treatment purposes is given in U.S. Pat. No. 5,589,458 (Jameson et al.), which is herein incorporated by reference.

The present invention provides pharmaceutical compositions that comprise the compounds of the invention and pharmaceutically acceptable carriers or diluents. Suitable pharmaceutical carriers are described in Remington's Pharmaceutical Sciences, A. Osol, a standard reference text in this field. The peptides of the present invention may be administered alone or in combination with other diagnostic, therapeutic or additional agents. Therapeutic agents may include cytokines or lymphokines, such as IL-2, α-interferon and interferon-γ. Additional agents may include excipients such as flavoring, coloring, stabilizing agents, thickening materials, osmotic agents and antibacterial agents. The treatments of the present invention may be combined with conventional therapies, which may be administered sequentially or simultaneously.

The pharmaceutical compositions of the present invention may be administered by any means that enables the active agent to reach the targeted cells. Because peptides are subject to digestion when administered orally, parenteral administration, i.e., intravenous, subcutaneous, intramuscular, would ordinarily be used to optimize delivery. The formulation of the present pharmaceutical composition will depend on the route of administration. Aerosol medicaments may be used for intranasal or inhalation administration. In some cases, topical administration may be desirable. Liposomal formulations may also be used.

When the compound is a nucleic acid, the pharmaceutical composition may be injected directly into a target tissue as described in U.S. Pat. No. 5,589,466. Alternatively, various strategies developed to accomplish cell or receptor-specific targeting of nucleic acids or vectors may also be used.

The dosage of compound administered will vary depending upon pharmacodynamic characteristics of the compound, its mode and route of administration, the age, health, and weight of the recipient, the nature and extent of the cancer, and any concurrent treatments. Usually, the dosage of peptide will be about 1 to 3000 milligrams per 50 kilograms of body weight; preferably 10 to 1000 milligrams per 50 kilograms of body weight; more preferably 25 to 800 milligrams per 50 kilograms of body weight. An effective DNA or mRNA dosage will generally be in the range from about 0.05 μg/kg to about 50 mg/kg. However, this dosage will vary in a manner apparent to these of skill in the art according to the activity of the peptide encoded by the nucleic acid and the efficiency of nucleic acid targeting and expression.

Other issues pertaining to dosage and administration will be apparent to one skilled in the art in view of the present disclosure.

The above disclosure generally describes the present invention. A more complete understanding can be obtained by reference to the following specific examples which are provided herein for purposes of illustration only, and are not intended to limit the scope of the invention.

EXAMPLE 1

CLIP Peptides and Anti CLIP Antibody

Truncated peptides from the rat MHC Class II invariant chain $V_0$: (sequence aa 82–103 PKSAKPVSPMRMATPLL-MRPLS (SEQ ID NO:1)), V1: aa 90–104 (SEQ ID NO:2), V2: 86–100 (SEQ ID NO:3), V3: 90–100(SEQ ID NO:4) were synthesized by Quality Controlled Biochemicals Co. (Hopkinton, Ma.) and purified by HPLC.[15,23] The peptides (>92% purity) were dissolved in RPMI 1640 prior to use. Force loading of CLIP was accomplished by incubating the cells in 10 μM of the peptide for 1 hr. at 4° C. Dose response studies revealed that maximal enhancement of lytic activity was achieved by pretreating the target cells with 1–10 μM of peptide. Antibody was prepared to the CLIP peptide by Quality Controlled Biochemicals Co. The peptides were conjugated to keyhole limpet hemocyanin (KLH). Rabbits were immunized with the peptide-KLH conjugate. The antibody was affinity purified using peptide conjugated sepharose matrix columns.

Truncated peptides from the human MHC Class II invariant chain (human sequence aa 82–103: PKPPKPVSKMRMATPLLMQALP(SEQ ID NO:6)) and the truncated variant containing the MHC Class II binding domain (aa 91–101: MRMATPLLMQA (SEQ ID NO:8)) were synthesized by Quality Controlled Biochemicals Co. (Hopkinton, Ma.) and purified by HPLC.[14-17] The peptides (>92% purity) were dissolved in RPMI 1640 prior to use. Force loading of CLIP was accomplished by incubating the cells in graded concentrations of the peptide for 2 hours at 4° C. Dose response studies revealed that maximal enhancement of lytic activity was achieved by pre-treating the target cells with $\geq 1$ μM of peptide. Binding was confirmed by flow cytometry using the rabbit anti-human CLIP antibody. Antibody was prepared to the CLIP peptide by Quality Controlled Biochemicals Co. The peptides were conjugated to keyhole limpet hemocyanin (KLH). Rabbits were immunized with the peptide-KLH conjugate. The antibody was affinity purified using peptide conjugated sepharose matrix columns. Fab fragments from the affinity purified antibody were prepared by limited papain digestion and sephadex G-200 column chromatography.[19] The specificity of the affinity purified polyclonal antibody was confirmed by Enzyme-linked immunosorbent assay (ELISA) comparing its ability to recognize the longer truncated CLIP ($V_{00}$, SEQ ID NO:5) and three shorter variants (V1, aa 82–103 (SEQ ID NO:6), V2, aa 90–110 (SEQ ID NO:7) and V3, aa 91–101 (SEQ ID NO:8)) containing either flanking region or just the MHC Class II binding domain. The polyclonal antibody recognized both flanking regions and the MHC Class II binding domain but did not recognize an irrelevant peptide. Moreover, addition of free excess CLIP or the variants but not the irrelevant peptide inhibited the ELISA. Murine monoclonal antibody to human CLIP was also obtained from Dr. Peter Cresswell, Yale University (New Haven, Conn.).

This monoclonal antibody recognized the N-terminal flanking region (aa 81–87) on CLIP.[20,21]

EXAMPLE 2

Flow Cytometry

Expression of MHC Class II determinants and CLIP were assessed flow cytometrically. The cells were stained with either murine anti-human MHC Class II antibodies or the rabbit anti-CLIP antibody for 1 hr. At 4° C., washed 2× in phosphate buffered saline and counter stained with FITC conjugated sheep anti-mouse IgG (absorbed with rat IgG; Sigma Chemical Co., St. Louis, Mo.) or FITC conjugated goat anti rabbit IgG (Sigma Chemical co.) for 1 hr at 4° C. as previously described.[13,18] As controls, the cells were incubated with normal mouse serum or rabbit prebleed IgG followed by counter staining with the FITC conjugated secondary reagents. After washing 2× in phosphate buffered saline, the cells were analyzed on an Coulter Epics 752 flow cytometer.

EXAMPLE 3

Recognition of CLIP in Rats

We first evaluated whether CLIP in rats is recognized by the autoreactive T cells associated with CsA-induced syngeneic GVHD by comparing the lysis of target cells after various pretreatment conditions. Pretreatment of the PHA lymphoblast target cells with antibody to CLIP completely blocked lysis mediated by the CsA induced autoreactive T cells (Table 1). Moreover, forced loading of CLIP onto the target cells markedly enhanced their susceptibility to recognition and lysis. Purification of the CD8+ Vβ8.5+ effector T-cell subset yielded comparable results. Spleen cells from control, non CsA-treated animals did not mediate significant lysis even when CLIP loaded target cells were used (data not shown).

TABLE 1

Recognition of CLIP in Rats by Syngeneic GVRD Effector T Cells

| | Effector T-cells | Target-Cell Pretreatment | % Specific Lysis of Target Cells |
|---|---|---|---|
| Group 1 | Syngeneic GVHD | Diluent | 19.2 ± 3.2 |
| | | Control peptide | 16.0 ± 4.1 |
| | | CLIP | 48.5 ± 6.9 |
| Group 2 | Syngeneic GVHD | Prebleed IgG | 23.6 ± 4.9 |
| | | Anti-CLIP | 1.4 ± 0.6 |

Both groups contained a 30:1 E:T ratio. Results in both groups represent the mean of three separate experiments.

EXAMPLE 4

Localization of CLIP Binding Domains in Rat

Since CLIP contains an MHC Class II binding domain and flanking regions that extend beyond the peptide binding groove of MHC Class II molecules, a series of studies was undertaken evaluating truncated variants of rat CLIP.[15,23] As shown in FIG. 5, force loading variant 2 (SEQ ID NO:3) containing the flanking regions defined by amino acids 86–91 markedly increased the susceptibility of the target cells to lysis mediated by the CsA induced autoreactive T lymphocytes. Force loading variant 1 (SEQ ID NO:2) containing flanking region defined by amino acids 99–104 inhibited recognition of the target cells presumably due to the displacement of endogenously expressed native CLIP. Force loading variant 3 (SEQ ID NO:4) that primarily contains the MHC Class II binding domain modestly inhibited lysis of the target cells. Although the unfractionated effector T cells appeared to preferentially recognize variant 2, clonal analysis by limiting dilution cultures revealed that in addition to CD8+Vβ8.5+ T cells (confirmed by RT-PCR[18]) that preferentially recognized CLIP variant 2, a subpopulation of autoreactive T cells could be isolated that selectively recognized variant 1.

EXAMPLE 5

Inhibition of Target Cell Recognition by SEB

The autoreactive T cells are highly restricted to a Vβ TcR element (Vβ8.5) that, in mice, defines a population of cells that is responsive to the superantigen staphylococcal enterotoxin β (SEB) (Table 2).[18] Based on the fact that CLIP can modify the T cell response to this superantigen,[17] SEB was assessed for its ability to inhibit the recognition of target cells by syngeneic GVHD autoreactive lymphocytes. Pretreatment of the effector T lymphocytes with SEB for one hour at 4° C. completely inhibited their ability to recognize and lyse the target cells. Comparatively, pretreatment of the target cells with this superantigen was ineffective at preventing recognition and lysis.

TABLE 2

Effect of Staphylococcal Enterotoxin B (SEB) on Autoreactive T-cell Recognition in Syngeneic GVHD

| Effector T-cells | Target Cells | % Specific Lysis |
|---|---|---|
| Diluent | Diluent | 68.4 |
| SEB pretreated | Diluent | 5.7 |
| Diluent | SEB pretreated | 49.8 |

E:T ratio was 30:1. Variation between replicate cultures averaged <10%.

EXAMPLE 6

Identification of Effector Cells

Studies were undertaken to characterize the effector cell population that mediated the autocytotoxicity. The results showed that depletion of cells expressing the α/β T cell receptor and the CD8 cell surface determinant eliminated the ability of PBMC from patients with autologous GVHD to lyse pretransplant lymphoblasts. Depletion of the CD4 subset of cells had only a minimal effect. In one patient, however, autocytoxic function was significantly eliminated (>70%) when the PBMC were depleted of either CD4 or CD8 cells. These results suggest either both CD4+ and CD8+ were required for killing or that the effector cell in this single patient expressed both cell surface accessory molecules.

EXAMPLE 7

Identification of Target Antigen

A series of antibody blocking studies was also performed in order to identify the antigen or restricting element recognized on the target cell by the autoreactive lymphocytes. The pretransplant lymphoblasts and the T47D breast cancer cell line were pretreated with $^{51}$Cr and monoclonal antibodies to either MHC Class I or MHC Class II determinants for one hour at 4° C. The cells were washed in RPMI 1640 prior to use as targets in the $^{51}$Cr release assay. The results detailed in Table 3 show that pre-treatment of both target cells with antibody to MHC Class II determinants significantly blocked lysis mediated by the PMBC from patients with autologous GVHD. On the other hand, MHC Class I antibodies were ineffective.

TABLE 3

Recognition of MHC Class II Determinants by Autocytotoxic T Cells Associated with Autologous GVHD

| | | % Specific Lysis of Treated Target Cells Mediated by Autologous GVHD Effector Lymphocytes Pretreatment of Target Cells | | |
|---|---|---|---|---|
| Target Cells | Serum | Normal Mouse Class I | Anti-MHC Class II | Anti-MHC |
| Autologous | Exp. 1 | 43.7 | 40.6 | 10.5 |
| Lymphoblasts | Exp. 2 | 23.7 | 21.3 | 5.4 |
| T47D | Exp. 1 | 28.7 | 29.6 | 4.9 |
| | Exp. 2 | 48.2 | NT$^A$ | 8.3 |

$^A$NT = not tested

EXAMPLE 8
CLIP and Target Cell Recognition

A series of studies was undertaken to determine whether CLIP was involved in the recognition of MHC Class II determinants by the autologous GVHD effector T cells.

Initially, the affinity purified antibody to CLIP was assessed for its ability to block lysis mediated by the autoreactive T cells derived from patients with autologous GVHD. Pretransplant lymphoblasts and T47D cells were labeled with $^{51}$Cr and with (1.5 μg) rabbit antibody to CLIP (Fab) or prebleed IgG for 1 hr at 4° C. prior to use as targets in a $^{51}$Cr release assay (Table 4). In every patient tested, lysis of pretransplant lymphoblasts and the T47D cell line was completely blocked by pretreatment of the target cells with the affinity purified anti-CLIP antibody. Blocking of lysis (>95% reduction) was confirmed in three patients using a murine monoclonal antibody to human CLIP that recognizes the N-termal flanking region (aa 81–87).[20,21] Moreover, addition of free excess CLIP (10 μM) but not an irrelevant peptide to the assay specifically inhibited the antibody from blocking recognition (data not shown). On the other hand, anti-CLIP antibody pretreatment of target cells did not block lysis mediated by allospecific cytolytic T cells sensitized in a mixed lymphocyte response (n=3, mean±S.D. 27.3±6.2% specific lysis of control mouse Ig treated target cells versus 25.9±5.4% specific lysis of anti-CLIP treated target cells at a 75:1 effector:target ratio).

TABLE 4

Recognition of Target Cells Pretreated with Anti-CLIP Antibody

| | % Specific Lysis of Treated Target Cells Mediated by the Autologous GVHD Effector Lymphocytes Pretreatment of Target Cells | |
|---|---|---|
| Target Cells | Control | Anti-CLIP |
| Autologous Lymphoblasts (n = 11) | 18.0 ± 3.9 | 1.5 ± 0.6 |
| T47D (n = 4) | 26.6 ± 6.5 | 0.5 ± 2.9 |

Effector to Target ratio was 100:1.

EXAMPLE 9
CLIP Expression

Expression of CLIP and MHC Class II determinants on the lymphoblasts and on the human T47D tumor cell line was assessed flow cytometrically. As shown in FIG. 2 approximately 25% of the MHC Class II positive lymphoblasts expressed significant levels of CLIP as detected by staining with the anti-CLIP antibody. The remainder of the lymphoblasts showed minimal staining with the anti-CLIP antibody indicating low expression of CLIP. Forced loading of CLIP (1 μM) not only resulted in an increase in the relative intensity of staining of the population but also led to a two to threefold increase in the number of cells that intensely stain with the anti-CLIP antibody (data not presented). Comparatively, the T47D cells which also expressed MHC Class II determinants, showed significant staining with the anti-CLIP antibody. CLIP expression on the tumor cell line as detected flow cytometrically, was more homogeneous compared to the lymphoblasts.

EXAMPLE 10
Enhancement of Lysis After Force Loading of CLIP

Since only a fraction of the autologous PHA blast cells expressed significant levels of CLIP, studies were undertaken to assess whether force loading of this peptide onto the target cells enhances their ability to be recognized and lysed by the autoreactive T lymphocytes. Pretransplant lymphocytes stimulated with PHA were incubated for 2 hours at 4° C. with 1 μM of CLIP and washed three times in RPMI 1640 prior to use as target cells in a $^5$Cr release assay. The results in Table 5 show that force loading of CLIP onto the PHA lymphoblast target cells significantly enhanced their susceptibility to lysis mediated by the autologous GVHD associated effector T cells. Lysis was enhanced two-fold after force loading of CLIP. Similarly, as shown in Table 5, lysis of the human T47D cell line by the autologous GVHD effector T cells was also enhanced by force loading of CLIP. In contrast, loading an irrelevant MHC Class II binding peptide did not enhance lysis.

TABLE 5

Susceptibility to Recognition and Lysis Mediated by the Autologous GVHD Effector Cells is Enhanced by Force Loading CLIP

| | 14 % Specific Lysis of Treated Target Cells | |
|---|---|---|
| Pretreatment | PHA Blast Cells | T47D Cells |
| CLIP Loaded (n = 3) | 30.2 ± 3.9 | 34.9 ± 2.7 |
| Control (n = 3) | 15.3 ± 12.1 | 16.4 ± 1.3 |

Effector to target ratio was 100:1.0

EXAMPLE 11
In vivo Antitumor Activity of SGVHD in Rats

Recent studies in our laboratory show SGVHD effector cells in rats have antitumor activity in vivo, achieving about a 1–2 log kill of CRL1662 myeloma cells. Thus, the magnitude of the immunologic antitumor activity generated by SGVHD appears to be similar to that produced by allogeneic GVHD.[26] Since SGVHD has little toxicity, enhancement the antitumor activity of this syndrome was examined for potential increases in therapeutic efficacy in vivo.

Nylon wool nonadherent spleen cells (50×10$^6$) from Lou M animals with syngeneic GVHD were adoptively transferred into secondary Lou M recipients (irradiated, bone marrow reconstituted) challenged with 2.5×10$^4$ CRL 1662 myeloma cells. Animals were treated with gamma-interferon (50,000 U/d), IL-2 (10,000 U/d), or a combination for ten days. Survival was assessed and log tumor cell kill was estimated from dose response studies (see Table 6).

One approach therefore was to amplify the autoreactive effector cells by the administration of IL-2. In fact, high-dose IL-2 (50,000–100,000 u/d) markedly exacerbates the clinical autoimmune syndrome in animals, leading to the death of all the animals treated with CsA and IL-2.[27,28] On the other hand, both interferon-$\gamma$[25] and interferon-$\alpha$ enhance the antitumor effect of SGVHD by 1–2 logs in the rat model, with cure of about half of animals given $5 \times 10^3$ tumor cells. This activity of the interferons in SGVHD appears to be mediated through increasing the expression of MHC class II determinants on the tumor, as the interferons have no direct activity on their own in this animal model. Moreover, resolution of the tumor was associated with the development of tumor-specific immunity as the rats were immune to rechallenge with the tumor after resolution of the SGVHD. Although high-dose IL-2 (50–100,000 u/d) markedly augments the severity of SGVHD, the addition of low-dose IL-2 to interferon produces significant enhancement of antitumor activity without an apparent increase in toxicity.[27,28] Low-dose (5–10,000 units/d) IL-2 alone has no immunomodulatory effects on CsA-induced SGVHD. This dose of IL-2, however, appears to have an additive effect when used in combination with interferon-$\gamma$, increasing the tumor cell kill by 1–2 logs compared to interferon-$\gamma$ alone. These data suggest that the antitumor activity of CsA-induced SGVHD can be enhanced by amplifying the autoreactive effector T cells and by upregulating the target antigen (MHC class II determinants) on the tumor cells, thereby potentiating tumor cell recognition and destruction.

TABLE 6

Antitumor Activity of Syngeneic GVHD and Potentiation by Cytokines following Adoptive Transfer of Effector T Cells

| | Treatment | Estimated Log Tumor Cell Kill |
|---|---|---|
| Syngeneic GVHD | effector cells + 0 | 1.5–2.0 |
| Syngeneic GVHD | effector cells + $\gamma$-interferon | 2.5–3.0 |
| Syngeneic GVHD | effector cells + IL-2 | 2.0–2.5 |
| Syngeneic GVHD | effector cells + $\gamma$-int + IL-2 | 4.0–4.5 |

EXAMPLE 12

Activity of CLIP Variants

We characterized the regions of CLIP that are required for the promiscuous recognition of MHC Class II determinants. The results from our studies reveal several important concepts. First, promiscuous recognition of MHC Class II determinants occurs at the clonal level and is critically dependent on CLIP. Pretreating both syngeneic and MHC disparate target cells with antibodies to MHC Class II determinants (but not MHC Class I antigens) or to CLIP blocked killing of the target cells mediated by V$\beta$8.5+ CD8+ T cell clones established from animals with auto GVHD. Second, recognition of the MHC Class II determinants by the autoreactive T cells requires both the MHC Class II binding domain and the N-terminal flanking region of CLIP. This N-terminal flanking region extends beyond the open termini of MHC Class II molecules and appears to interact near the staphylococcal enterotoxin B (SEB) binding site of the V$\beta$ segment of the T cell receptor (TcR). This interaction strengthens the TcR-CLIP-MHC Class II complex, decreasing the off time, thus, maximizing recognition and lysis.

Our results also explain the restriction of the T cell repertoire to lymphocytes expressing the V$\beta$8.5 TcR segment. Third, V$\beta$8.5+ CD8+ clones requiring this interaction were the pathogenic T cells in vivo confirmed in a local GVHR foot pad assay. Injection of these cells in vivo resulted in histological changes (dyskeratosis) consistent with GVHD. We have identified the amino acid sequence on CLIP responsible for the interaction with V$\beta$ segment of the TcR. Our studies reveal the sequence to be -KPVSP- (residues 5–9 of SEQ ID NO:1), although VSP is sufficient, and -PKSAKPVSP- (residues 1–9 of SEQ ID NO:1) works even better.

TABLE 7

Activity of CLIP Variants

| Clip Variants | Enhancement of Target Cell Recognition |
|---|---|
| PKSAKPVSP(MRMATPLLMR)PLS(residues 1–22 of SEQ ID NO:1) | ++++ |
| PKSAKPVSP(R)(residues 1–19 of SEQ ID NO:1) | +++ |
| KPCSP(R)(residues 5–19 of SEQ ID NO:1) | +++ |
| PVSP(R)(residues 6–19 of SEQ ID NO:1) | +++ |
| VSP(R)(residues 7–19 of SEQ ID NO:1) | +++ |
| SP(R)(residues 8–19 of SEQ ID NO:1) | 0 |

Target cells were loaded with the CLIP variants (10 uM) and evaluated for their ability to be lysed by syngeneic GVHD effector T cells. Lytic activity was compared to control diluent treated target cells with enhancement representing at least a >25% increase in specific killing. R = MRMATPLLMR (residues 10–19 of SEQ ID NO:1) which is therat MHC class II binding domain. The corresponding human sequence is R = MRMATPLLMQ (residues 10–19 SEQ ID NO:5). The human corresponding N-flanking region is PKPPKPVSK (residues 1–9 of SEQ ID NO:6). The human C-terminal flanking region is ALPMGALPQG (residues 20–29 of SEQ ID NO:5). The rat C-terminal flanking region is PLSMDNMLQA (residues 20–29 of SEQ ID NO:1).

EXAMPLE 13
CLIP Enhances Tumor Cell Kill

Studies to evaluate the ability of peptides from the MHC Class II invariant chain to augment tumor cell recognition in the auto GVHD setting were initiated. Our results clearly indicate that CLIP can enhance autoreactive T lymphocytes mediated tumor cell kill.

Following induction of auto GVHD, animals were challenged intraperitoneally with $2.5 \times 10^4$ CRL1666 tumor cells (MHC Class II+). Subsequently parent CLIP, or two truncated variants (V1: MHC Class II domain plus C-terminal flanking region; V2: MHC Class II domain plus N-terminal flanking region) were administered intraperitoneally (100 µg). Animals treated with the parent peptide (2/3) or variant V2 (3/3) survived beyond 50 days. In contrast, animals receiving the control diluent or variant V1 all succumbed to tumor growth by day 25. Previous tumor cell dose response studies suggest our results are consistent with an additional 1–2 log tumor cell kill. Importantly, these peptides did not significantly enhance the clinical manifestations of auto GVHD. Interestingly, the activity of the peptides in the tumor model paralleled the CLIP specificity of the effector T cells summarized above.

TABLE 8

Administration of clip variants enhances antitumor activity of syngeneic gvhd

| CLIP VARIANTS | SURVIVAL (days) |
| --- | --- |
| 0 | 23, 23 |
| Parent | 22, >50, >50 |
| Variant 1 (MHC class II binding domain + C-terminus) | 22, 22, 25 |
| Variant 2 (MHC class II binding domain + N-terminus) | >50, >50, >50 |

Syngeneic BMT recipients were challenged intraperitoneally with $2.5 \times 10^4$ tumor cells the day after cessation of CsA treatment. Subsequently, 100 µg of the CLIP variant peptides were administered intraperitoneally.

EXAMPLE 14
Chimeric Peptides

We evaluated whether addition of the -KPVSP- peptide fragment could potentiate the recognition of target cells expressing another MHC class II binding peptide by the syngeneic GVHD effector T cells. The BN allopeptide (sequence identified in FIG. 3 (SEQ ID NO: 14)) from BN strain rats that binds to Lewis rat MHC class II antigens was modified by the addition of the KVSP fragment (SEQ ID NO:1). The BN allopeptide (derived from MHC class I molecules) is one of the peptides conferring allorecognition of BN rats by Lewis strain animals.

Lewis target cells were loaded with either the parent BN allopeptide or the chimeric construct and evaluated for their susceptibility to killing mediated by 15 syngeneic GVHD effector clones. As shown in FIG. 3, there was minimal to no recognition of target cells loaded with the unmodified BN allopeptide. In contrast target cells loaded with the chimeric peptide were effectively lysed by the autoreactive T cell clones.

Addition of the KPVSP (SEQ ID NO:1) fragment potentiated recognition of the target cells overriding restriction normally conferred by the MHC class II allopeptide complex Animals were immunized (2x, subcutaneous) with the chimeric construct. The animals received BN skin grafts. Control animals receiving diluent rejected the BN skin grafts were a survival of 13 days. Skin graft survival, however, was only 8–9 days in the animals immunized with the chimeric construct suggesting that immunity was heightened.

REFERENCES

1. Hess, A. D. Syngeneic/Autologous Graft-vs-Host Disease: Mobilization of Autoimmune Mechanisms as Antitumor Immunotherapy. Cancer Control 1:201, 1994.
2. Hess, A D. Autologous Graft-Versus-Host Disease: A Novel Approach for Antitumor Immunotherapy. Human Immunology 34:219, 1992.
3. Jones R J, Vogelsang G B, Hess A D, Farmer E R, Mann R B, Geller R B, Piantadosi S. Santos, G W. Induction of graft-versus-host disease after autologous bone marrow transplantation. Lancet 1:754, 1989.
4. Hess A D, Horwitz L R, Beschorner W E, Santos G W. Development of GVHD-like Syndrome in CsA-Treated Rats after Syngeneic BMT. J. Exp. Med. 161:718, 1985.
5. Jenkins M K, Schwartz R H, Pardoll D M. Effects of cyclosporine A on T cell development and clonal deletion. Science 241:1655, 1988.
6. Geller R B, Esa A H, Beschorner W E, Frondoza C G, Santos G W, Hess A D. Successful in vitro graft-versus-tumor effect against an Ia-bearing tumor using cyclosporine-induced syngeneic graft-versus-host disease in the rat. Blood 74:1165, 1989.
7. Noga S J, Horwitz L, Kim H, Laulis M K. & Hess, A D. Interferon-γ potentiates the antitumor effect of cyclosporine-induced autoimmunity. Journal of Hematotherapy 1:75, 1992.
8. Jones R J, Kennedy M J, Hess A D. Autologous Graft-vs-Host Disease. Bone Marrow Trans. 15(suppl. 1), S119, 1995.
9. Kennedy M J, Vogensang G B, Beveridge R A, Farmer E R, Altomonte V, Huelskamp A M, Davidson N E. Phase I trial of intravenous cyclosporine to induce graft-versus-host disease in women undergoing autologous bone marrow transplantation for breast cancer. J. Clin. Oncol. 11:478, 1993.
10. Yeager A M, Vogelsang G B, Jones R J, Farmer E R, Altomonte V, Hess A D, Santos G W. Induction of cutaneous graft-versus-host disease by administration of cyclosporine to patients undergoing autologous bone marrow transplantation for acute myeloid leukemia. Blood 79:3031, 1992.
11. Kennedy M J, Vogelsang G B, Jones R J, Farmer E R, Hess A D, Altomonte V, Huelskamp A M, Davidson N E. Phase I Trial of Interferon-Gamma to Potentiate Cyclosporine A-Induced Graft-Versus-Host Disease in Women Undergoing Autologous Bone Marrow Transplantation for Breast Cancer. J. Clin. Oncol. 12, 249–257 (1994).
12. Kennedy M J, Beveridge R A, Rowley S D, Gordon G B, Abeloff M D, Davidson N E. High-dose chemotherapy with reinfusion of purged autologous bone marrow following dose-intense induction as initial therapy for metastatic breast cancer. J Natl Cancer Inst. 83:920, 1991.
13. Ruvolo P P, Bright E C, Kennedy M J, Morris L E, Fischer A C, Vogelsang G B, Jones R J, Hess A D. Cyclosporine-induced autologous graft-versus-host disease: Assessment of cytolytic effector mechanisms and the Vβ T cell receptor repertoire. Transpl. Proc. 27:1363, 1995.
14. Malcherek G, Gnau V, Jung G, Rammensee H G, Melms A. Supermotifs Enable Natural Invariant Chain-Derived Peptides to Interact with Many Major Histocompatibility Complex Class II Molecules. J. Exp. Med. 181:527, 1995.
15. Freisewinkel I M, Schench K, Koch N. The Segment of the Invariant Chain that is Critical for Association with Major Histocompatibility Complex Class II Molecules Contains the Sequence of a Peptide Eluted from Class II Polypeptides. Proc. Natl. Acad. Sci. USA 90:9703, 1993.
16. Chicz R M, Urban R G, Gorga J C, Vignali D A, Lane W S, Strominger J L. Specificity and promiscuity among naturally processed peptides bound to HLA-DR alleles. J. Exp. Med. 178:27, 1993.
17. Ericson M L, Sundstrom M, Sansom D M, Charron D J. Mutually exclusive binding of peptide and invariant chain to major histocompatibility complex class II antigens. J. Biol. Chem. 269:26531, 1994.
18. Fischer A C, Ruvolo, P P, Burt R, Horwitz L R, Bright E C, Hess J M, Beschorner W E, Hess A D. Characterization of the autoreactive T cell repertoire in cyclosporine-induced syngeneic graft-versus-host disease: A highly conserved repertoire mediates autoaggression. J. Immunol. 154:3713, 1995.
19. Parham, P. On the fragmentation of monoclonal IgG1, IgG2a, and IgG2b from BALB/c mice. J. Immunol. 131:2895, 1983.
20. Riberdy, J M, Newcomb, J R, Surman, M J, Balbosa, J A, Cresswell, P. HLA-DR Molecules from an Antigen-processing Mutant Cell Line are associated with Invaiant Chain Peptides. Nature 360:474, 1992.
21. Cresswell, P. Assembly, Transport and Function of MHC class II Molecules. Ann. Rev. Immunol 12:259, 1994.
22. Dayhof M D: Nat. Biomed. Res. Found., Washington, D.C. Vol. 5, suppl. 3, 1978.
23. Malcherek G V, Gnau V, Jung G, et al: J Exp Med 181: 527, 1993.
24. Vogelsang G B, Hess A D, Altomonte V, Bitton R, Horn T, Jones R J. Interferon augmentation of autologous graft-vs-host disease (GVHD). Blood 1996;88(Suppl.) :129a.
25. Noga S J, Horwitz L, Kim H, Laulis M K, Hess A D. Interferon-γ potentiates the antitumor effect of cyclosporine-induced autoimmunity. Journal of Hematotherapy 1:75–84, 1992.
26. Hageenbeek A, Martens A C M, Schultz F W. The graft-versus-leukemia reaction after allogeneic bone marrow transplantation only adds one log of leukemia cell kill. Blood 72:390a, 1988.(Abstract)
27. Hess, A D, Kennedy, M J, Ruvolo, P P, Vogelsang, G B, and Jones, R J. Antitumor Activity of Syngeneic/Autologous Graft-vs-Host Disease. Annals of The New York Academy of Sciences, in press, 1995.
28. Hess, A D, and Noga, S J. Cyclosporine Induced Syngeneic Graft-vs-Host Disease: An immunotherapeutic approach after autologous bone marrow transplantation. Int. J. of Cell Cloning, 10 (Suppl 1):179–182, 1992.

What is claimed is:

1. A polypeptide comprising a first and second segment, wherein the first segment consists of contiguous amino acid residues of the invariant chain of MHC class II selected from SEQ ID NO: 1 and comprises the sequence VSP, and wherein the second segment comprises an antigen.

2. The polypeptide of claim 1 wherein the first segment comprises the sequence PVSP (residues 6–9 of SEQ ID NO:1).

3. The polypeptide of claim 1 wherein the first segment comprises the sequence KPVSP (residues 5–9 of SEQ ID NO:1).

4. The polypeptide of claim 1 wherein the first segment comprises the sequence PKSAKPVSP (residues 1–9 of SEQ ID NO:1).

5. The polypeptide of claim 1 wherein the antigen is a viral antigen.

6. The polypeptide of claim 1 wherein the antigen is allopeptide.

7. The polypeptide of claim 1 wherein the antigen is a tumor associated antigen.

8. The polypeptide of claim 1 wherein the antigen is her2/neu.

9. A polypeptide comprising a first and second segment, wherein the first segment consists of contiguous amino acid residues of the invariant chain of MHC class II selected from SEQ ID NO: 5 and comprises the sequence VSK, and wherein the second segment comprises an antigen.

10. The polypeptide of claim 9 wherein the first segment comprises the sequence PVSK (residues 2–5 of SEQ ID NO:11).

11. The polypeptide of claim 9 wherein the first segment comprises the sequence KPVSK (residues 1–5 of SEQ ID NO:11).

12. The polypeptide of claim 9 wherein the first segment comprises the sequence PKPPKPVSK (residues 1–4 of SEQ ID NO:6).

13. The polypeptide of claim 9 wherein the antigen is a viral antigen.

14. The polypeptide of claim 9 wherein the antigen is allopeptide.

15. The polypeptide of claim 9 wherein the antigen is a tumor associated antigten.

16. The polypeptide of claim 9 wherein the antigen is her2/neu.

17. A polypeptide consisting of a segment of the invariant chain of MHC class II which contains 3 to 28 contiguous amino acid residues selected from SEQ ID NO: 1 and comprises the sequence VSP.

18. The polypeptide of claim 17 which comprises the sequence PVSP (residues 6–9 of SEQ ID NO:1).

19. The polypeptide of claim 17 which comprises the sequence KPVSP (residues 5–9 of SEQ ID NO:1).

20. The polypeptide of claim 17 which comprises the sequence PKSAKPVSP residues 1–9 of SEQ ID NO:1.

21. A method of modulating an immune response, comprising:
contacting T cells with a polypeptide comprising a segment of the invariant chain of MHC class II, wherein the segment consists of 3 to 29 contiguous amino acid residues selected from SEQ ID NO: 1 and comprises the sequence VSP.

22. The method of claim 21, wherein the polypeptide consists of 29 amino acids as shown in SEQ ID NO: 1.

23. The method of claim 21 wherein the polypeptide comprises a second polypeptide segment.

24. The method of claim 21 wherein the polypeptide is expressed in dendritic cells which have been transfected with a recombinant construct.

25. The method of claim 24 wherein the dendritic cells are administered to a mammal subsequent to transfection.

26. A method of modulating an immune response, comprising:
contacting T cells with a polypeptide comprising a first segment of the invariant chain of MHC class II, wherein the first segment contains 3 to 28 contiguous amino acid residues selected from SEQ ID NO: 5 and comprises the sequence VSK wherein the polypeptide comprises a second segment comprising an antigen.

27. The method of claim 26 wherein the first segment consists of 28 amino acids as shown in SEQ ID NO: 5.

28. The method of claim 26 wherein the polypeptide is expressed in dendritic cells which have been transfected with a recombinant construct.

29. The method of claim 28 wherein the dendritic cells are administered to a mammal subsequent to transfection.

30. The method of claim 26 wherein the first segment consists of 3 to 29 contiguous amino acid residues as shown in SEQ ID NO: 1.

31. The method of claim 26 wherein the first segment consists of 29 amino acids as shown in SEQ ID NO: 5.

32. A vaccine for inducing an immune response to an antigen comprising a polypeptide comprising a first and second segment, wherein the first segment consists of contiguous amino acid residues of the invariant chain of MHC class II selected from SEQ ID NO: 1 and comprises the sequence VSP, and wherein the second segment comprises an antigen, said polypeptide being suspended in a pharmaceutically acceptable carrier.

33. The vaccine of claim 32 further comprising an adjuvant.

34. A vaccine for inducing an immune response to an antigen comprising a polypeptide comprising a first and second segment, wherein the first segment consists of contiguous amino acid residues of the invariant chain of MHC class II selected from SEQ ID NO: 5 and comprises the sequence VSK, and wherein the second segment comprises an antigen, said polypeptide being suspended in a pharmaceutically acceptable carrier.

35. The vaccine of claim 34 further comprising an adjuvant.

36. A polypeptide comprising a segment of the invariant chain of MHC class II wherein the segment comprises residues 1–6 and 10–29 as shown in SEQ ID NO:1 and does not contain the sequence VSP.

37. A polypeptide comprising a segment of the invariant chain of MHC class II, wherein the segment comprises residues 1–6 and 10–29 as shown in SEQ ID NO:5 and does not comprise the sequence VSK.

38. A method of modulating an immune response, comprising:

contacting T cells with a polypeptide comprising a segment of the invariant chain of MHC class II, wherein the segment comprises residues 1–6 and 10–29 as shown in SEQ ID NO:5 and does not contain the sequence VSP.

39. A method of modulating an immune response, comprising:

contacting T cells with a polypeptide comprising a segment of the invariant chain of MHC class II, wherein the segment comprises residues 1–6 and 10–29 as shown in SEQ ID NO:5 and does not contain the sequence VSK.

* * * * *

UNITED STATES PATENT AND TRADEMARK OFFICE
CERTIFICATE OF CORRECTION

PATENT NO.   : 6,326,465 B1
DATED        : December 4, 2001
INVENTOR(S)  : Allan Hess It is certified that error appears in the above-identified patent and that said Letters Patent is hereby corrected as shown below:

<u>Column 25,</u>
Line 44, "residues 1-4" has been replaced with -- residues 1-9 --.

Signed and Sealed this

Twenty-sixth Day of November, 2002

Attest:

Attesting Officer

JAMES E. ROGAN
*Director of the United States Patent and Trademark Office*

```
                         SEQUENCE LISTING

<160> NUMBER OF SEQ ID NOS:  17

<210> SEQ ID NO 1
<211> LENGTH: 29
<212> TYPE: PRT
<213> ORGANISM: Rattus rattus

<400> SEQUENCE: 1

Pro Lys Ser Ala Lys Pro Val Ser Pro Met Arg Met Ala Thr Pro Leu
1               5                   10                  15

Leu Met Arg Pro Leu Ser Met Asp Asn Met Leu Gln Ala
            20                  25

<210> SEQ ID NO 2
<211> LENGTH: 15
<212> TYPE: PRT
<213> ORGANISM: Rattus rattus

<400> SEQUENCE: 2

Pro Met Arg Met Ala Thr Pro Leu Leu Met Arg Pro Leu Ser Met
1               5                   10                  15

<210> SEQ ID NO 3
<211> LENGTH: 15
<212> TYPE: PRT
<213> ORGANISM: Rattus rattus

<400> SEQUENCE: 3

Lys Pro Val Ser Pro Met Arg Met Ala Thr Pro Leu Leu Met Arg
1               5                   10                  15

<210> SEQ ID NO 4
<211> LENGTH: 11
<212> TYPE: PRT
<213> ORGANISM: Rattus rattus
```

<400> SEQUENCE: 4

Pro Met Arg Met Ala Thr Pro Leu Leu Met Arg
1               5                   10

<210> SEQ ID NO 5
<211> LENGTH: 29
<212> TYPE: PRT
<213> ORGANISM: Homo sapiens

<400> SEQUENCE: 5

Pro Lys Pro Pro Lys Pro Val Ser Lys Met Arg Met Ala Thr Pro Leu
1               5                   10                  15

Leu Met Gln Ala Leu Pro Met Gly Ala Leu Pro Gln Gly
            20                  25

<210> SEQ ID NO 6
<211> LENGTH: 22
<212> TYPE: PRT
<213> ORGANISM: Homo sapiens

<400> SEQUENCE: 6

Pro Lys Pro Pro Lys Pro Val Ser Lys Met Arg Met Ala Thr Pro Leu
1               5                   10                  15

Leu Met Gln Ala Leu Pro
            20

<210> SEQ ID NO 7
<211> LENGTH: 21
<212> TYPE: PRT
<213> ORGANISM: Homo sapiens

<400> SEQUENCE: 7

Lys Met Arg Met Ala Thr Pro Leu Leu Met Gln Ala Leu Pro Met Gly
1               5                   10                  15

Ala Leu Pro Gln Gly
            20

<210> SEQ ID NO 8
<211> LENGTH: 11
<212> TYPE: PRT
<213> ORGANISM: Homo sapiens

<400> SEQUENCE: 8

Met Arg Met Ala Thr Pro Leu Leu Met Gln Ala
1               5                   10

<210> SEQ ID NO 9
<211> LENGTH: 6
<212> TYPE: PRT
<213> ORGANISM: Rattus rattus

<400> SEQUENCE: 9

Lys Pro Val Ser Pro Met
1               5

<210> SEQ ID NO 10
<211> LENGTH: 6
<212> TYPE: PRT
<213> ORGANISM: Rattus rattus

<400> SEQUENCE: 10

Met Arg Pro Leu Ser Met

-continued

<210> SEQ ID NO 11
<211> LENGTH: 6
<212> TYPE: PRT
<213> ORGANISM: Homo sapiens

<400> SEQUENCE: 11

Lys Pro Val Ser Lys Met
 1               5

<210> SEQ ID NO 12
<211> LENGTH: 7
<212> TYPE: PRT
<213> ORGANISM: Homo sapiens

<400> SEQUENCE: 12

Met Gly Ala Leu Pro Gln Gly
 1               5

<210> SEQ ID NO 13
<211> LENGTH: 6
<212> TYPE: PRT
<213> ORGANISM: Homo sapiens

<400> SEQUENCE: 13

Met Gln Ala Leu Pro Met
 1               5

<210> SEQ ID NO 14
<211> LENGTH: 17
<212> TYPE: PRT
<213> ORGANISM: Rattus rattus

<400> SEQUENCE: 14

Lys Pro Val Ser Pro Met Leu Ile Tyr Asn Arg Glu Glu Tyr Ala Arg
 1               5                  10                  15

Phe

<210> SEQ ID NO 15
<211> LENGTH: 11
<212> TYPE: PRT
<213> ORGANISM: Rattus rattus

<400> SEQUENCE: 15

Leu Ile Tyr Asn Arg Glu Glu Tyr Ala Arg Phe
 1               5                  10

<210> SEQ ID NO 16
<211> LENGTH: 1287
<212> TYPE: DNA
<213> ORGANISM: Homo sapiens

<400> SEQUENCE: 16
ctgcaggggg ggggggggg ggggggaca ttggctcttc cttggggagt gatgcacagg      60
aggagaagca ggagctgtcg ggaagatcag aagccagtca tggatgacca gcgcgacctt     120
atctccaaca atgagcaact gcccatgctg gccggcgcc ctgggccccc ggagagcaag     180
tgcagccgcg gagccctgta cacaggcttt tccatcctgg tgactctgct cctcgctggc     240
caggccacca ccgcctactt cctgtaccag cagcagggcc ggctggacaa actgacagtc     300
acctcccaga acctgcagct ggagaacctg cgcatgaagc ttcccaagcc tcccaagcct     360

-continued

| | |
|---|---|
| gtgagcaaga tgcgcatggc caccccgctg ctgatgcagg cgctgcccat gggagccctg | 420 |
| ccccagggc ccatgcagaa tgccaccaag tatggcaaca tgacagagga ccatgtgatg | 480 |
| cacctgctcc agaatgctga ccccctgaag gtgtacccgc cactgaaggg gagcttcccg | 540 |
| gagaacctga gacaccttaa gaacaccatg agaccatag actggaaggt ctttgagagc | 600 |
| tggatgcacc attggctcct gtttgaaatg agcaggcact ccttggagca aaagcccact | 660 |
| gacgctccac cgaaagagtc actggaactg gaggacccgt cttctgggct gggtgtgacc | 720 |
| aagcaggatc tgggcccagt ccccatgtga gcagcagag ggcggtcttc aacatcctgc | 780 |
| cagccccaca cagctacagc tttcttgctc ccttcagccc ccagcccctc ccccatctcc | 840 |
| caccctgtac ctcatcccat gagacccctgg tgcctggctc tttcgtcacc cttggacaag | 900 |
| acaaaccaag tcggaacagc agataacaat gcagcaaggc cctgctgccc aatctccatc | 960 |
| tgtcaacagg ggcgtgaggt cccaggaagt ggccaaaagc tagacagatc cccgttcctg | 1020 |
| acatcacagc agcctccaac acaaggctcc aagacctagg ctcatggacg agatgggaag | 1080 |
| gcacagggag aagggataac cctacaccca gaccccaggc tggacatgct gactgtcctc | 1140 |
| tcccctccag cctttggcct tggcttttct agcctattta cctgcaggct gagccactct | 1200 |
| cttccctttc cccagcatca ctccccaagg aagagccaat gttttccacc catccctccc | 1260 |
| cccccccccc cccccccccc cctgcag | 1287 |

<210> SEQ ID NO 17
<211> LENGTH: 1353
<212> TYPE: DNA
<213> ORGANISM: Rattus rattus

<400> SEQUENCE: 17

| | |
|---|---|
| cagcagcagc agcagcagca gcaccagcag cacttggggg aaaagctaga ggctagagtc | 60 |
| atggatgacc agcgcgacct catctctaac catgagcagc tgcccatcct gggccagcgt | 120 |
| gctagagccc agaaagcaa ttgcaaccgt ggagtcctgt acaccagtgt ctctgtcctg | 180 |
| gtggctctgc tcttggctgg gcaggccacc actgcttact cctgtacca gcagcagggc | 240 |
| cgcctggaca agctgaccgt cacctcccag aacctgcaac tggagaacct tcgcatgaag | 300 |
| cttccgaaat ctgccaaacc tgtgagcccg atgcgcatgg ctactccctt gctgatgcgc | 360 |
| ccactgtcca tggataacat gctccaagcg cccgtgaaga atgttaccaa gtatggcaac | 420 |
| atgacccagg accacgtgat gcacctgctt acgaagtctg acccgtgaa ctacccacag | 480 |
| ctgaagggga gcttcccgga gaatctgaag caccttaaga actctatgaa tggtctggac | 540 |
| tggaaggtct ttgagagctg gatgaaacag tggctgttgt ttgaaatgag caagaactcc | 600 |
| ctggaggaga agcagcccac ccagactcca cctaaagtat tgaccaagtg ccaggaagaa | 660 |
| gtcagccaca tccctgatgt ccaccccggg gcgttccgtc ccaagtgtga tgagaacggt | 720 |
| aactatatgc cactccagtg ccatgggagc actggctact gctggtgtgt gttccccaac | 780 |
| ggcactgagg tccctcacac caagagccgc gggcgccata actgcagtga gccactggac | 840 |
| atggaagacc catcttctgg cctgggagtg accaagcagg atatgggcca aatgttcttg | 900 |
| tgaagacaga agccagctct gcacggcggc agctcccctg ctcctcagcc cttcttacac | 960 |
| tccctaacat cacaccccat ttcccgtctt cctgcaccct ggggcttgag actggtatct | 1020 |
| gcttcaccgt ccctggacac aacaaatgaa accggaacag aatgagaaca ctggagggag | 1080 |
| ggccttgctg cctaccccca tctaagggac ccccatttct gacccattag cagtctttaa | 1140 |
| tgtggggctc tgagatctag gcccactgac agggataggg gatgccctac ccttaatcta | 1200 |

```
ggctggatac atttgctgtc ttctcaagga agaggccaag ccctcccagc aaccttcct    1260 catgtcctgc cgacgccct gggatccctg ctcagccaag cttgtcagca gcctgtagga   1320
ccatggttca cgtgacaata aaggtagaa ggt                                  1353
```